United States Patent
DiFilippo et al.

[19]

[11] Patent Number: 5,969,358
[45] Date of Patent: Oct. 19, 1999

[54] WHOLE BODY SCAN COINCIDENCE IMAGING

[75] Inventors: Frank P. DiFilippo, University Heights; Mark H. Heller, Garfield Heights; Robert L. Zahn, Chagrin Falls, all of Ohio

[73] Assignee: Picker International, Inc., Highland Heights, Ohio

[21] Appl. No.: 08/977,231

[22] Filed: Nov. 24, 1997

Related U.S. Application Data

[60] Provisional application No. 60/031,810, Nov. 26, 1996.

[51] Int. Cl.$^6$ .......................... G01T 1/166; G01T 1/169
[52] U.S. Cl. ........................................ 250/363.03
[58] Field of Search ......................... 250/363.03

[56] References Cited

U.S. PATENT DOCUMENTS

| | | |
|---|---|---|
| 4,746,795 | 5/1988 | Stewart et al. . |
| 4,983,841 | 1/1991 | Stewart . |
| 5,093,575 | 3/1992 | Perusek . |
| 5,097,132 | 3/1992 | Plummer . |
| 5,296,709 | 3/1994 | Jarkewicz . |
| 5,331,553 | 7/1994 | Muehllehner et al. . |
| 5,532,489 | 7/1996 | Yamashita et al. . |
| 5,569,924 | 10/1996 | Plummer . |
| 5,591,977 | 1/1997 | Green et al. . |
| 5,602,395 | 2/1997 | Nellemann et al. . |
| 5,608,221 | 3/1997 | Bertelsen et al. . |
| 5,663,566 | 9/1997 | Maniawski et al. . |

FOREIGN PATENT DOCUMENTS

| | | |
|---|---|---|
| 2 052 205 | 1/1981 | United Kingdom . |
| WO 95/35509 | 12/1995 | WIPO . |
| WO 97/21113 | 6/1997 | WIPO . |

OTHER PUBLICATIONS

Pamphlet: "The Prism Opportunity"; No. 22965/1090/B459; 1990 Picker International, Inc.
Brochure: "Prism the new standard in imaging"; Ohio Imaging 1989.
Brochure: "Prism 2000XP Dual–Head Nuclear Medicine Imaging"; PD2081 R996 1996 Picker International, Inc.
Brochure: "Prism 3000XP Three–Head Nuclear Medicine Imaging"; BR2082 296 1996 Picker International, Inc.
Brochure: "Prism 2000XP Dual–Head Nuclear Medicine Imaging"; No. BR2081 1293 1993 Picker International, Inc.
Brochure: "Prism 2000XP Dual–Head Nuclear Medicine Imaging"; No. BR2081 R695 1995 Picker International, Inc.
Brochure: "Prism 3000XP Three–Head Nuclear Medicine Imaging"; No. BR2082 1293 1993 Picker International, Inc.
United States Statutory Invention Registration; Reg. No. H12 Published Jan. 7, 1986; Bennett, et al.; Nuclear Medicine Imaging System.

*Primary Examiner*—Constantine Hannaher
*Assistant Examiner*—Andrew Israel
*Attorney, Agent, or Firm*—Timothy B. Gurin; John J. Fry

[57] ABSTRACT

An imaging apparatus includes a pair radiation sensitive detector heads disposed on opposite sides of the patient. The detectors and patient are moved relative to each other in an axial direction while the relative angular orientation of the detectors and the patient is held constant. Positron annihilation events occurring within the anatomy of a patient are detected and used to reconstruct an image. According to one reconstruction technique, a focal plane method is used. The intersections of the lines of coincidence and a plurality of image planes is determined, and a series of images indicative of the intersections is generated.

15 Claims, 3 Drawing Sheets

007
WHOLE BODY SCAN COINCIDENCE IMAGING

This application claims priority to provisional U.S. Application Ser. No. 60/031,810, filed Nov. 26, 1996.

BACKGROUND

The present invention relates to the art of nuclear medicine, and particularly to the art of positron coincidence detection (PCD).

Positron emission tomography (PET) is a branch of nuclear medicine in which a positron-emitting radiopharmaceutical such as $^{18}$F-fluorodeoxyglucose (FDG) is introduced into the body of a patient. Each emitted positron reacts with an electron in what is known as an annihilation event, thereby generating a coincident pair of 511 keV gamma rays which travel in opposite directions along what is known as a line of coincidence. The coincident pair is detected and used to create a clinically useful image.

Traditionally, PET scanners have used detector elements arranged in circles or rings about the imaging region, with a plane of the rings perpendicular to the axis of the imaging region. Each ring corresponds to an axial slice of the patient. Data from each ring of a plurality of slices is reconstructed using a two or three dimensional reconstruction algorithms to create images of the patient.

The demand for PET has been steadily increasing. The positron emitting pharmaceutical FDG may be the most important nuclear imaging agent to date because of its ability to tag malignant tumors. It is highly desirable to screen patients from head to toe or toe to head for suspected tumors using FDG prior to performing more localized PET or other imaging techniques. However, the potential of PET imaging as a general screening tool cannot be fully realized because conventional PET imaging systems have a small axial field of view (generally less than 150 mm) and are very expensive (ranging from $1.2 to $2.9 million).

The development of large field of view multiple head gamma detector systems capable of performing positron coincidence imaging offers a more cost effective alternative to conventional PET imaging systems. This invention addresses the practical implementation of whole body PET imaging using large field of view gamma detector systems.

SUMMARY

According to a first aspect of the present invention, a method of imaging utilizing a plurality of detectors disposed about an imaging region so as to detect coincident gamma ray pairs generated by position annihilation events occurring with an object in the imaging region is provided. Each detector has a radiation sensitive face and is capable of detecting radiation received at a plurality of axial and transverse coordinates on its face. The method includes detecting coincident gamma ray pairs, determining an axial and a transverse coordinate at which each gamma ray in a plurality of the coincident gamma ray pairs was detected, and utilizing the determined coordinates to generate an image indicative of the positron annihilation events. The detectors and the object are maintained at a constant relative angular orientation while the coincident gamma ray pairs are detected.

According to a more limited aspect, the detectors and object are moved relative to each other in an axial direction. Fore each of the plurality of detected gamma ray pairs, the relative axial position of the detectors and the patient is determined. The determined coordinates and the determined relative axial positions are used to generate an image indicative of the positron annihilation events. During the steps of detecting and moving, the detectors and the object are maintained at a constant relative angular orientation.

According to a more limited aspect, two detectors disposed about the image region in an opposed relationship are utilized.

According to another more limited aspect, the step of utilizing comprises the step of performing one of a back-projection technique and an iterative reconstruction technique.

According to yet another more limited aspect, the step of utilizing includes defining an image plane. For each of a plurality of the detected gamma ray pairs, an intersection of the line of coincidence and the image plane is determined.

According to a still more limited aspect of the present invention, the object has a longitudinal axis and the plane is substantially parallel to the longitudinal axis.

According another still more limited aspect, a plurality of spaced apart image planes may be defined. For each of the pluraltiy of image plane, an image indicative of the intersections is be determined.

According to another aspect of the present invention, an imaging method includes the steps of detecting positron annihilation events occurring within the anatomy of a patient and defining an image plane. For each of a plurality of the detected events, the intersection of the line of coincidence and the image plane is determined. An image indicative of the intersections of the lines of coincidence and the image plane is generated.

According to a more limited aspect of the invention, the image plane is substantially parallel to the longitudinal axis of the patient.

According to a still more limited aspect, the method includes the steps of defining a plurality of spaced apart image planes, determining for each of the plurality of image planes the intersections of the lines of coincidence and the image plane, and for each of the plurality of image planes, generating an image indicative of the intersections. The spacing between the planes may be 10 mm.

According to another more limited aspect, the events are detected using a plurality of detectors, each detector comprising a plurality of light sensitive elements arranged in a matrix extending in longitudinal and transverse directions.

According to a still more limited aspect of the invention, the detectors and the patient are moved relative to each other in an axial direction and the axial position of the detectors relative to the patient is determined.

According to another more limited aspect, the step of defining is performed prior to the step of detecting.

According to another aspect, an imaging apparatus includes a means for detecting a plurality of position annihilation events occurring within the anatomy of a patient, means for determining the intersecting of each of the lines of coincidence and an image plane, and means for generating an image indicative of the intersection of the of each of the lines of coincidence and the image plane.

A first advantage of the present invention is that substantially whole body PET images may be obtained rapidly and inexpensively.

Yet another advantage of the present invention is that the effective axial field of view of the detectors may extend over substantially the entire length of the patient.

Still other advantages will be appreciated by those skilled in the art upon reading and understanding the appended description.

DRAWINGS

DESCRIPTION

Figure 1:
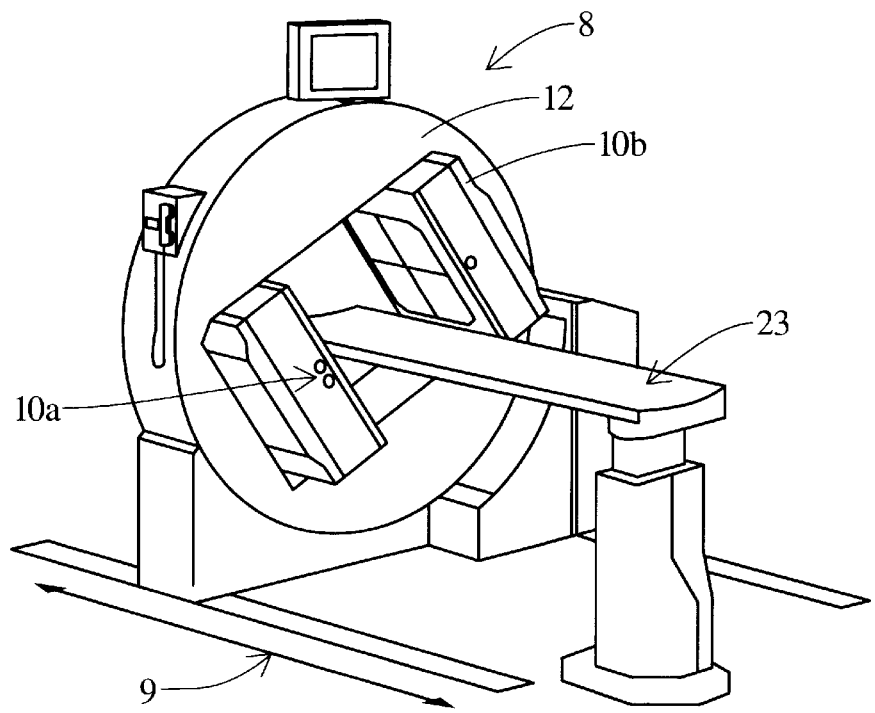
FIG. 1 is a perspective view of a nuclear camera according to the present invention.

With reference to FIG. 1, a nuclear camera 8 includes a gantry assembly 12 and a pair of opposed detector heads 10a, 10b. A patient table 23 is adapted to support a patient or other object being imaged. The detector heads 10 are physically mounted to the mechanical gantry assembly 12 in such a way as to allow the object being imaged to be placed between the opposing detector 10 surfaces. FIG. 1 shows an example of a nuclear camera 8 in which the gantry 12 and detector heads 10 move in the axial direction 9 while the scanned object maintains a fixed position.

The detector heads 10a, 10b are rectangular position sensitive gamma ray detectors configured such that at least two of the detector heads 10 can be physically located to detect positron event activity. The electrical outputs of the detector heads 10 specify the x,y coordinates of events detected on the detector surfaces, and the energy, or z, of the events. An electronic subsystem determines whether events have been received by both detector heads within a narrow time window, also described as being in coincidence. Event validity is also tested to insure that the coincidence pair is complete and in coincidence. Event discrimination (energy windowing) is also performed to ensure that the detected events are within an energy range consistent with the radionuclide being used. The coincident data is then transferred to a real time data acquisition and processing system.

In order to perform a head to toe survey of the patient, either the gantry assembly 12 supporting the detectors 10 or the object being imaged must be moved in a controlled fashion along a whole body or axial axis of movement 9 so that all of the desired area to be imaged is positioned for an equal amount of time in the field of view of the detectors 10, which is generally physically smaller in the axial direction than the object or patient being imaged.

Figure 4:
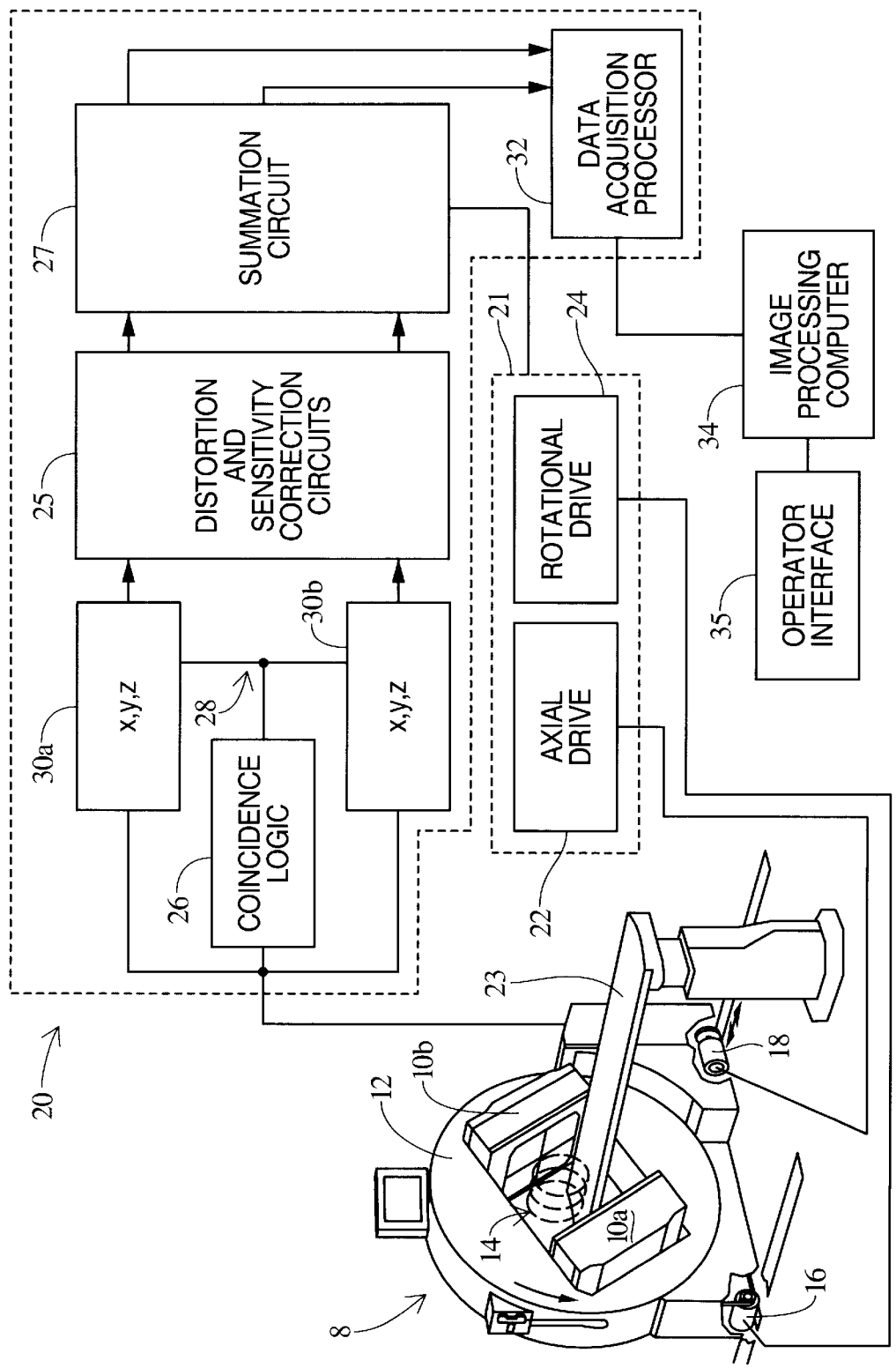
FIG. 4 is a block diagram of an imaging system according to the present invention.

It is vital that the motion relationship of the gantry, the detector heads 10 and the object or patient be precisely controlled in order to produce accurate images. With reference to FIG. 4, this is accomplished by use of a precision motion control system 21, which is used to either move the gantry 12 and hence the detector system 10 over the scanned object or move the platform or table 23 supporting the scanned object or patient through the gantry 12 and detectors 10, ensuring that all areas of the scanned object receives equal time in the detector field of view during the whole body survey. The motion control system 21 includes a high precision positional encoder, which is used by the motion control system 21 to determine both axial positional and speed information.

With continuing reference to FIG. 4, the gamma camera 8 includes gamma camera heads 10a, 10b mounted to move rotationally and axially with respect to an examination region 14. Radiation emanating from or passing through the subject is detected by the gamma camera heads 10a, 10b. Although described with respect to two gamma camera heads 10a, 10b, three or more heads can also be used.

The heads 10a, 10b are mounted to a rotating gantry portion 12. The gamma camera 8 also includes a rotational motive means such as motor 16 and an axial motive means such as motor 18 which can be operated alone or in combination in order to move the detector heads 10a, 10b to a plurality of positions with respect to the examination region 14. The rail mounted gantry and hence the detectors 10a, 10b can be translated axially along the examination region 14 and rotated about the examination region 14 in a generally circular path.

The motion control system 21 also includes axial drive 22 and rotational drive 24 for controlling the operation of the motors 16, 18. Associated with each drive is a position feedback device such as a position encoder. Accordingly, drives 22 and 24 provide closed-loop control of the rotational and axial positions. Relative axial motion between the detectors 10a, 10b and the patient can alternately be accomplished by translating the patient support 23.

Each detector head 10 includes a NaI(T1) scintillator crystal layer and x,y array of photomultiplier tubes (PMTs). Energy from gamma rays striking the scintillator crystal is converted to light which is detected by one or more of the PMTs, thereby signaling a detected event. Coincidence logic circuitry 26 determines whether events are detected by both detectors 10a, 10b simultaneously. More specifically, the coincidence logic 26 determines whether both detectors detect a gamma ray within a predetermined coincidence time interval, for example on the order of 15 nanoseconds. If so, the coincidence logic 26 generates a digital coincidence signal 28 which indicates that a coincidence event has occurred. If, on the other hand, the detectors 10a, 10b detect events which are separated in time by more than the coincidence time interval, the coincidence signal 28 is not generated, and the events are not processed further.

Associated with each detector 10a, 10b is energy and position determining circuitry 30a, 30b which determines both the energy z and position x,y of the detected events. The circuitry 30a, 30b is triggered by the coincidence signal 28 such that the energy z and position x,y is determined only for coincident events. For each coincidence event, positions and energies $x_1, y_1, z_1$ and $x_2, y_2, z_2$ are generated corresponding to the events detected by the detectors 10a, 10b. The positions $y_1, y_2$ in the axial direction are adjusted to account for the axial position of the detector heads 10 at the time the coincident event is detected. Stated another way, the y positions are determined with respect to the patient or imaging region.

A data acquisition processor 32 receives the data for each detected event and generates a list which includes the energy z and position x,y of the detected events in each of a plurality of coincidence event pairs, together with the rotational position θ of the detector at the time the coincidence event is detected. This information is preferably stored for processing at a convenient time, for example after data acquisition for a particular patient has been completed.

Further processing of the stored data is preferably accomplished using a conventional imaging computer 34. The data is reconstructed as described more fully below. An operator interface 35 preferably includes a video processor and monitor or printer for converting selected portions of the images into human readable form.

With ongoing reference to FIG. 4, the position x,y and energy z event data generated by the detectors 10 is provided to distortion and sensitivity correction circuitry 25, where the data is corrected for various detector geometric distortions and sensitivity variations. Corrected event data is in turn provided to summation circuitry 27. Positional information from the motion control system 21 is also provided to the summation circuitry 27. The summation circuitry 27 sums event positional information with positional information from the axial position encoder, thereby producing a summed x,y,z output for each detected event.

Figure 2:
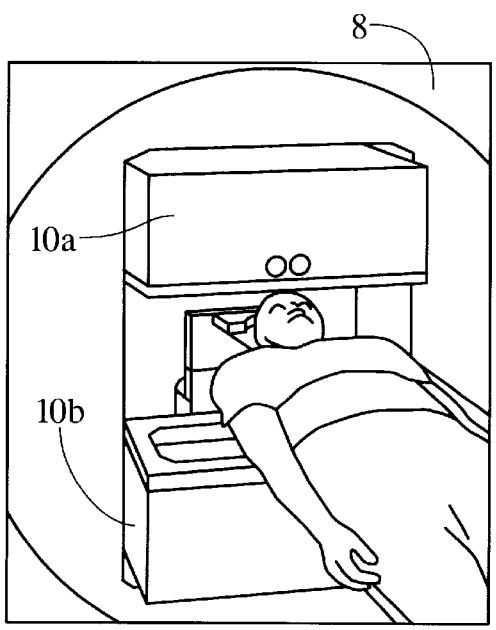
FIG. 2 depicts a typical detector/patient positioning at the start of a whole body imaging survey.
Figure 3:
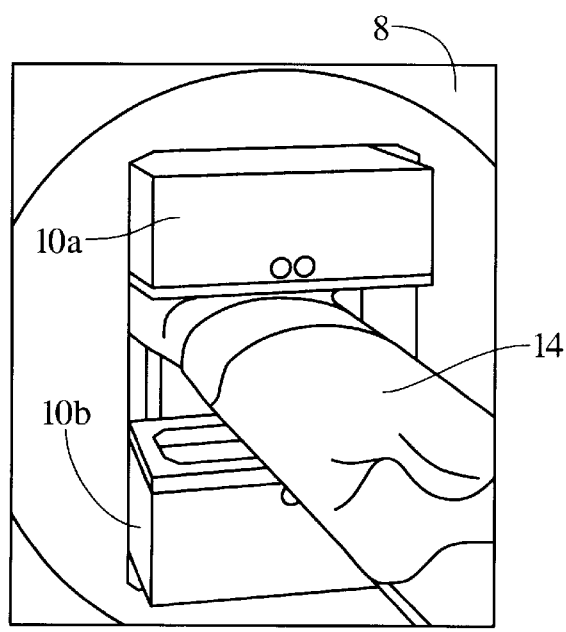
FIG. 3 depicts a typical detector/patient positioning as a whole body imaging survey progresses.

During a whole body scan, the detector heads 10 remain at the same transverse angle θ while they are slowly moved in the axial direction 9 from head to toe. FIG. 2 shows an example of the detector position for a study where the scan begins at the head of the patient 14 (i.e., at the start of a whole body survey), while FIG. 3 shows the detector position somewhat later in that study as the study progresses and the detectors 10 move relative to the patient. The operation of such a system is not limited to head to toe imaging, but can scan in either direction with user definable start and end positions.

The output of the axial position encoder is also supplied to the summation circuitry 27 during the survey. As the detector heads 10 move relative to the scanned object, the positional difference from the original to the current detector head 10 location is tracked by the real time data acquisition system 20. This positional difference value is summed with the event positional information supplied by the detector heads for the moving axis. The summation may occur either on an event by event basis or after the completion of the study. This process creates a detector field of view with an axial dimension limited only by the mechanical travel of the detector heads relative to the scanned object. Stated another way, a the system creates a virtually unlimited detector field of view in the axial direction by use of a high precision motion control system coupled with the electronic capability to sum the detector physical position relative to the object being scanned with the positional positron event data location as recorded by the detectors.

This summed event data is then processed and reconstructed to generate an image indicative of the anatomy of the patient. This processing and reconstruction can be performed on an event by event basis or as a batch process at the end of the study.

For collimated (single-photon) imaging, data is collected at only one angle of incidence, perpendicular to the detector head. However, for coincidence imaging, data is collected at a range of axial and transverse angles, since collimation is done electronically instead of physically. Several angular views are acquired from the same detector position, there is depth information available in coincidence imaging that is not available for single photon imaging.

The simplest form of image reconstruction for such a system is focal plane imaging. Planar images are produced by backprojecting the lines of coincidence onto a specified plane. Each line that intersects with the plane forms a dot, and the superposition of all the dots forms the planar image.

Figure 5:
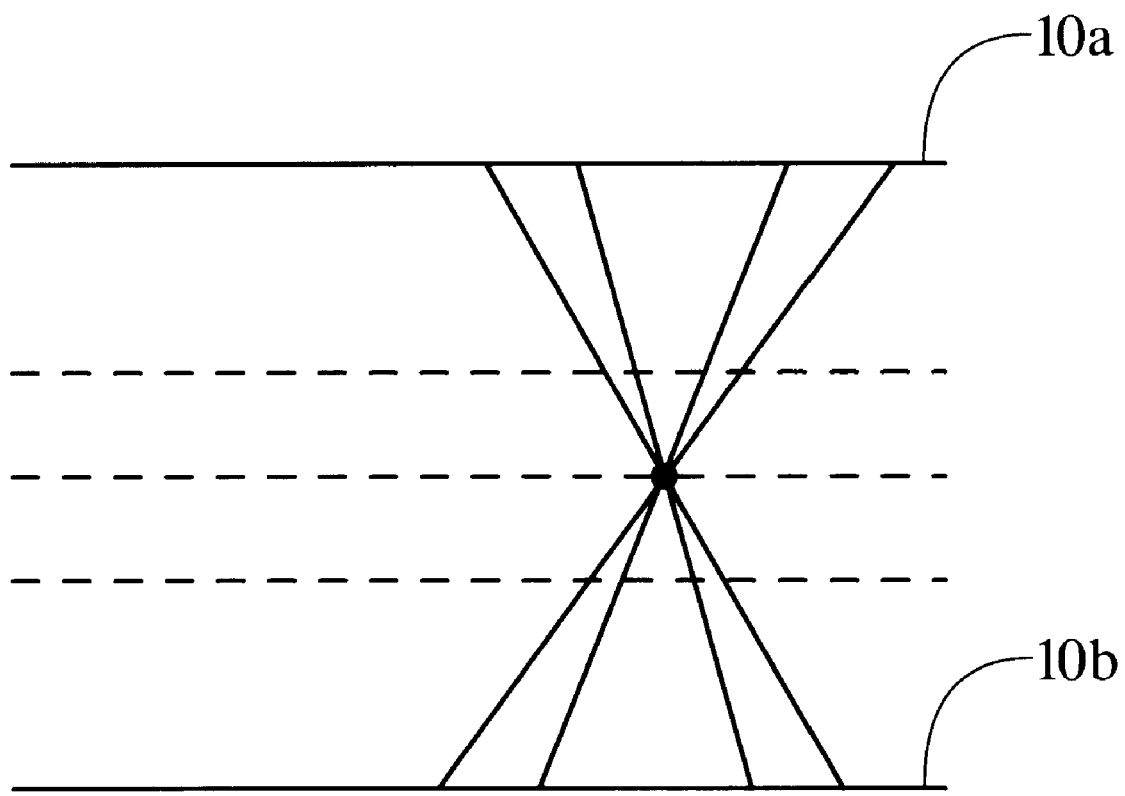
FIG. 5 illustrates the intersections of lines and coincidence and a plurality of imaging planes according to the present invention.

As illustrated by the dashed lines in FIG. 5, a series of planar images can be reconstructed at different depths between the detector heads 10. While each volume of activity is projected in several planes, it is only in focus in the plane intersecting the volume. In the other planes, the activity is present, but it is blurred. In addition to determining the horizontal position of the activity, this method also determines the vertical position (depth), since there is only one plane where the activity of interest is in focus. The ability to see the activity of interest is limited by the presence of activity above and below, whose counts are also contained in the same plane but are blurred out, reducing the image contrast.

This type of imaging is especially useful for whole body surveys for active tumors using FDG as the radiopharmaceutical. The uptake of FDG by tumors is much larger than by normal tissue, by approximately a 8:1 ratio. Presence or absence of active tumors can be quickly determined by a whole body scan. If a suspicious lesion is found, a second tomographic acquisition could be performed at this location for a better diagnosis.

An FDG whole body study was produced in accordance with the foregoing technique. The subject was a postsurgical colorectal cancer patient, and the goal of the survey was to determine whether any cancer remained in the pelvis and whether any cancer had spread to other parts of the body. The images produced were coronal planar views at various depths (spaced 15 mm apart), reconstructed by the method described above. A lesion in the chest region was readily visible in the plane in which the lesion was in focus. In neighboring planes, the lesion was still visible but not sharply in focus, and in other planes, the lesion was barely visible at all. Simply by inspecting the series of whole body images, a quick determination can be made of the extent to which cancer had spread. Suitable results have also been achieved with the planar views spaced apart by 10 mm.

To potentially improve image quality, the acceptance angle may be restricted in both the axial and transverse directions. The contrast would be improved by limiting the angular range, since less activity at other depths would be blurred into the plane of interest. However, this is achieved at the expense of a reduced number of counts and a reduced depth resolution. The angular range would therefore be chosen to optimize the image quality. One way to limit the acceptance angle in the axial direction is to mount septa (made of lead, for example) on the detector heads. Not only do the septa block out wide-angle events from reaching the detector, they also prevent radiation from other body parts with high activity (such as the bladder) from reaching the detector, reducing random coincidences and further improving the image contrast.

As with tomographic coincident imaging, it is also necessary to perform efficiency normalization in the transverse direction. The edges of the field of view have a lower sensitivity compared to the center of the field of view, since a smaller angular range can be seen by the detector. The planar image needs to be rescaled accordingly to make the count density more uniform and accurate across the field of view.

There are also other possible embodiments to whole body scan coincidence imaging. For example, the reconstructed planes do not have to be parallel to the detector heads, nor do the detector heads need to be parallel to each other. The radial positions of the detector heads could be adjusted as they are scanned laterally, as is commonly done in single-photon whole body imaging. More advanced methods of image reconstruction could be performed to improve the final image quality, such as maximum likelihood iterative reconstruction or limited angle tomographic reconstruction. Also, postprocessing the images with smoothing and/or restorative filters and correcting the images for random and scatter coincidences and detector non-uniformity could be employed.

The invention has been described with reference to the preferred embodiment. Obviously, modifications and alterations will occur to others upon reading an understanding Having described the preferred embodiment, the invention is now claimed to be:

1. A method of imaging utilizing a plurality of detectors disposed about an imaging region so as to detect coincident gamma ray pairs generated by positron annihilation events occurring within an object in the imaging region, each detector having a radiation sensitive face, each detector capable of detecting radiation received at a plurality of axial and transverse coordinates on the face thereof, the method comprising the steps of:

translating the detectors and the object relative to each other in the axial direction;

detecting coincident gamma ray pairs generated by positron annihilation events occurring within the object;

determining an axial and a transverse coordinate at which each gamma ray in a plurality of the detected coincident gamma rays pairs was detected;

for each of the plurality of the detected gamma ray pairs, determining the relative axial position of the detectors and the object; and utilizing the determined coordinates and the determined relative axial positions to generate an image indicative of the positron annihilation events;

wherein, during the steps of detecting and translating, the detectors and the object are maintained at a constant relative angular orientation.

2. The method of claim 1 utilizing two detectors disposed about the imaging region in an opposed relationship.

3. The method of claim 1 wherein the step of utilizing comprises the step of performing one of a backprojection technique and an iterative reconstruction technique.

4. The method of claim 1 wherein the coincident gamma rays travel in opposite directions along a line of coincidence and wherein the step of utilizing comprises:

defining an image plane;

for each of a plurality of the detected gamma ray pairs, determining an intersection of the line of coincidence and the image plane; and generating an image indicative of the intersections of the lines of coincidence and the image plane.

5. The method of claim 4 wherein the object has a longitudinal axis and the image plane is substantially parallel to the longitudinal axis.

6. The method of claim 4 further comprising the steps of:

defining a plurality of spaced apart image planes;

for each of the plurality of image planes, generating an image indicative of the intersections.

7. The method of claim 1 wherein each detector comprises a plurality of light sensitive elements disposed in a generally planar array.

8. A method of imaging comprising the steps of:

while maintaining a plurality of detectors, each detector including a plurality of light sensitive elements arranged in a planar array extending in axial and transverse directions, and a patient at a constant relative angular orientation, translating the detectors and the object relative to each other in the axial direction;

detecting positron annihilation events occurring within the anatomy of a patient, each positron annihilation event generating a pair of gamma rays traveling in opposite directions along a line of coincidence;

defining an image plane;

for each of a plurality of the detected events, determining an intersection of the line of coincidence and the image plane; and generating an image indicative of the intersections of the lines of coincidence and the image plane.

9. The method of claim 8 wherein the image plane is substantially parallel to the longitudinal axis of the patient.

10. The method of claim 9 further comprising:

defining a plurality of spaced apart image planes;

for each of the plurality of image planes, determining the intersections of the lines of coincidence and the image plane; and for each of the plurality of image planes, generating an image indicative of the intersections.

11. The method of claim 10 wherein the spacing between the image planes is 10 mm.

12. The method of claim 8 wherein the step of defining is performed prior to the step of detecting.

13. An imaging apparatus comprising:

means for detecting a plurality of positron annihilation events occurring within the anatomy of a patient, each positron annihilation event generating a pair of gamma rays traveling in opposite directions along a line of coincidence;

means for translating the means for detecting and the patient with respect to each other in an axial direction;

means for determining the relative axial position of the detectors and the patient;

means in operative communication with the means for detecting and the means for determining the relative axial position for determining the intersection of each of the lines of coincidence and an image plane; and means for generating an image indicative of the intersection of each of the lines of coincidence and the image plane.

14. The apparatus of claim 13 wherein the image plane is parallel to the longitudinal axis of the patient.

15. The apparatus of claim 13 wherein the means for detecting comprises a plurality of sensor heads, each sensor head including a plurality of light sensitive elements disposed in an array which extends in axial and transverse directions.

* * * * *